(12) United States Patent
Jakobsen et al.

(10) Patent No.: US 10,359,437 B2
(45) Date of Patent: Jul. 23, 2019

(54) BAG CONTAINING A REFERENCE FLUID

(71) Applicant: Radiometer Medical ApS, Bronshoj (DK)

(72) Inventors: Hans Peter Blaabjerg Jakobsen, Roedovre (DK); Torben Rydahl, Frederikssund (DK)

(73) Assignee: Radiometer Medical ApS, Bronshoj (DK)

(*) Notice: Subject to any disclaimer, the term of this patent is extended or adjusted under 35 U.S.C. 154(b) by 0 days.

(21) Appl. No.: 15/378,247

(22) Filed: Dec. 14, 2016

(65) Prior Publication Data
US 2017/0168072 A1 Jun. 15, 2017

(30) Foreign Application Priority Data
Dec. 15, 2015 (DK) .................. 2015 00805

(51) Int. Cl.
*B01L 3/00* (2006.01)
*B32B 27/08* (2006.01)
(Continued)

(52) U.S. Cl.
CPC .............. *G01N 33/70* (2013.01); *B01L 3/505* (2013.01); *B01L 3/523* (2013.01); *B32B 27/08* (2013.01);
(Continued)

(58) Field of Classification Search
CPC ...... G01N 33/70; G01N 2496/00; G01N 7/00; G01N 33/96; G01N 2496/70; B65D 33/02; B65D 51/002; B65D 31/04; B65D 75/5883; B65D 75/5827; B65D 75/30; B65D 75/008; B65D 75/52; B65D 65/42; B65D 81/2023; B65D 5/4204; B65D 1/0246; B65D 1/0215; B65D 5/563; B65D 65/40; B65D 75/58; B65D 65/38; B65D 75/40; B65D 75/26; B31B 70/84; B31B 70/60; B31B 70/64; B31B 2160/20;
(Continued)

(56) References Cited

U.S. PATENT DOCUMENTS 3,442,686 A   5/1969  Jones
5,725,958 A   3/1998  Matsuda
(Continued)

FOREIGN PATENT DOCUMENTS

CN   101688860 A   3/2010
EP   0 460 796 A2   12/1991
(Continued)

OTHER PUBLICATIONS

English language abstract of JP 08-090689, Apr. 9, 1996.
(Continued)

*Primary Examiner* — Lore R Jarrett
(74) *Attorney, Agent, or Firm* — Finnegan, Henderson, Farabow, Garrett & Dunner, LLP

(57) ABSTRACT

A sealed bag containing a reference fluid for the calibration and/or quality control of a creatine and/or creatinine sensor, the bag comprising: an inner polymer layer and an outer polymer layer; and an aluminium oxide gas barrier layer there between; and wherein the inner polymer layer is in contact with the reference fluid.

25 Claims, 6 Drawing Sheets

(51) Int. Cl.
  *B32B 27/32* (2006.01)
  *B32B 27/34* (2006.01)
  *B32B 27/36* (2006.01)
  *B32B 27/40* (2006.01)
  *B65D 30/08* (2006.01)
  *B65D 33/02* (2006.01)
  *B65D 51/00* (2006.01)
  *B65D 75/26* (2006.01)
  *G01N 33/70* (2006.01)

(52) U.S. Cl.
  CPC .............. *B32B 27/32* (2013.01); *B32B 27/34* (2013.01); *B32B 27/365* (2013.01); *B32B 27/40* (2013.01); *B65D 31/04* (2013.01); *B65D 33/02* (2013.01); *B65D 51/002* (2013.01); *B65D 75/26* (2013.01); *B01L 2300/044* (2013.01); *B01L 2300/0887* (2013.01); *B32B 2255/10* (2013.01); *B32B 2255/20* (2013.01); *B32B 2307/518* (2013.01); *B32B 2307/7242* (2013.01); *B32B 2307/7244* (2013.01); *B32B 2307/732* (2013.01); *B32B 2439/46* (2013.01); *B32B 2439/80* (2013.01); *G01N 2496/00* (2013.01)

(58) Field of Classification Search
  CPC . B31B 70/844; C09D 7/1216; H01L 31/0504; A61J 1/10; B01L 3/505; B01L 2300/04; B01L 2300/0848; B01L 2200/025; B01L 3/50; B01L 3/50825; B01L 2300/041; B01L 2200/026; B01L 2300/044; B01L 2200/0689; B01L 3/523; B01L 2300/0887; A61M 37/0015; A61M 5/14248; A61M 37/00; A61F 13/02; B81B 2201/055; A61B 17/205; B32B 2255/20; B32B 2255/10; B32B 2307/518; B32B 2307/7242; B32B 2307/7244; B32B 2439/46; B32B 2439/80; B32B 2307/732; B32B 27/40; B32B 27/08; B32B 27/32; B32B 27/34; B32B 27/365
  See application file for complete search history.

(56) References Cited

U.S. PATENT DOCUMENTS

| | | | |
|---|---|---|---|
| 5,777,202 | A | 7/1998 | Betts |
| 5,830,545 | A | 11/1998 | Frisk |
| 5,856,017 | A * | 1/1999 | Matsuda ................. B32B 15/08 428/446 |
| 9,101,936 | B2 | 8/2015 | Marcher et al. |
| 2003/0211261 | A1 | 11/2003 | Philips et al. |
| 2004/0161177 | A1 | 8/2004 | N'Dia |
| 2006/0013744 | A1 | 1/2006 | Mikkelsen et al. |
| 2008/0279487 | A1* | 11/2008 | Marcher ................. B01L 3/505 383/200 |
| 2013/0209003 | A1 | 8/2013 | Hansen et al. |
| 2013/0277391 | A1* | 10/2013 | Snowwhite .......... B65D 35/242 222/82 |
| 2015/0055895 | A1 | 2/2015 | Kishi et al. |

FOREIGN PATENT DOCUMENTS

| | | |
|---|---|---|
| EP | 1757533 A1 | 2/2007 |
| JP | H05179033 A | 7/1993 |
| JP | H05186622 A | 7/1993 |
| JP | H05214135 A | 8/1993 |
| JP | 08-090689 | 4/1996 |
| JP | H11221874 A | 8/1999 |
| JP | 2000508592 A | 7/2000 |
| JP | 2002-200108 | 7/2002 |
| JP | 2007-290269 | 11/2007 |
| JP | 2010-525339 | 7/2010 |
| WO | WO 97/08561 A1 | 3/1997 |
| WO | WO 97/16309 | 5/1997 |
| WO | WO 2008/131768 A1 | 11/2008 |
| WO | WO 2018/184902 A1 | 10/2018 |

OTHER PUBLICATIONS

English language abstract of JP 2007-290269, Nov. 8, 2007.
European Search Report for European Patent Application No. EP 16 20 3151, dated Apr. 25, 2017.
C.F.Struller, "Aluminum oxide barrier films on polymeric web and their conversation for packaging applications," 153-156, Oct. 27, 2013, Thin Solid Films.†

* cited by examiner
† cited by third party

BAG CONTAINING A REFERENCE FLUID

This application claims priority to Danish Patent Application No. PA 2015 00805, filed Dec. 15, 2015. The contents of this application is incorporated herein by reference.

FIELD OF THE INVENTION

The invention relates to a sealed bag containing a reference fluid for the calibration and/or quality control of a creatine and/or creatinine sensor.

BACKGROUND

Bags for reference fluids are widely used in connection with analytical instruments. The bags are frequently delivered in containers, e.g. a cassette, wherein several bags are delivered in one cassette.

It is common for reference fluid bags to contain gases such as $CO_2$ and $O_2$. Therefore, it is necessary for a reference fluid bag to be a sealed unit such that gas cannot enter or escape the contents of the bag, i.e. there is no fluid communication between the interior and exterior of the bag. This is important so that the relative concentrations of components, particularly gaseous components, in the bag are kept at the desired concentration.

An object of the invention is to provide an improved reference fluid bag for the calibration and/or quality control of a creatine and/or creatinine sensor. In particular, it is an object of the invention to provide a reference fluid bag resulting in improved calibration and/or quality control of a creatine and/or creatinine sensor.

SUMMARY OF THE INVENTION

According to a first aspect of the invention, there is provided a sealed bag containing a reference fluid for the calibration and/or quality control of a creatine and/or creatinine sensor, wherein the bag comprises an inner polymer layer and an outer polymer layer; and an aluminum oxide gas barrier layer there between; and wherein the inner polymer layer is in contact with the reference fluid. It has been surprisingly found that the sensitivity of a creatine and/or creatinine sensor can be established with significantly improved (i.e. greater) consistency when using a bag having an aluminum oxide layer according to the invention than when using a comparable bag having an aluminum gas barrier layer.

According to a second aspect of the invention, there is provided a creatine and/or creatinine sensor assembly for calibration and/or quality control, wherein the assembly comprises a sealed bag according to the first aspect of the invention; an access system comprising an access probe; and a creatine and/or creatinine sensor.

According to a third aspect of the invention, there is provided a reference fluid bag assembly comprising a sealed bag according the first aspect of the invention, which is adapted for being pierced by an access probe for withdrawal of the reference fluid; an access system; wherein the access system comprises a sealing element provided outside the bag and preventing any leakage between the bag and an access probe when the access probe has penetrated the bag, and a longitudinal support element provided inside the bag extending essentially parallel to an edge of the bag and being adapted to support the bag when the bag is penetrated by the access probe.

As detailed above, this invention relates to a sealed bag containing a reference fluid. The reference fluid contained within the sealed bag is for the calibration and/or quality control of a creatine and/or creatinine sensor. The following detailed description describes features of the sealed bag, i.e. the material from which the sealed bag is made from.

The term "sealed" is to be understood as meaning there is substantially no fluid communication between the interior and exterior of the bag. In other words, it is not possible for liquid to escape from or enter the bag.

The material from which the sealed bag is made comprises an inner polymer layer, an outer polymer layer and an aluminum oxide layer positioned there between. The inner polymer layer is in contact with the reference fluid. The sealed bag is flexible.

The inner polymer layer may be made of a polyolefin, such as polypropylene or polyethylene. It is preferred that the inner layer is made of polyethylene. It is also preferred that the inner polymer layer is bi-axially orientated. In a preferred embodiment, the inner polymer layer is bi-axially orientated polyethylene. The inner polymer layer may have a thickness of from 70 to 90 µm, preferably 75 to 85 µm.

The outer polymer layer may be any suitable polymer. Examples of suitable polymers include polyolefins, polyesters, polyurethanes, polycarbonates and polyamides. Preferably, the outer polymer layer is bi-axially orientated. Preferably, the outer polymer layer is bi-axially orientated polyamide. The thickness of the outer polymer layer may be from 10 to 20 µm, preferably 12 to 18 µm. The inclusion of this layer ensures proper mechanical stability of the bag.

The aluminum oxide layer provides a gas barrier. Therefore, it is called a aluminum oxide gas barrier layer. The aluminum oxide layer provides gas tightness and strength to the bag, i.e. to the material from which the bag is made. The thickness of the aluminum oxide layer may be from 40 to 60 nm, preferably 45 to 55 nm.

The bag may further comprise a first additional polymer layer which is positioned between the inner polymer layer and the outer polymer layer. Preferably, the first additional polymer layer is positioned between the outer polymer layer and the aluminum oxide layer, such that the aluminum oxide layer is placed adjacent to the inner polymer layer. This results in the aluminum oxide layer shielding the first additional polymer layer from the reference fluid.

The bag may further comprise a second additional polymer layer and a further aluminum oxide layer. The second additional polymer layer and further aluminum oxide layer are positioned between the outer polymer layer and the first additional polymer layer. Alternatively, the second additional polymer layer and the further aluminum oxide layer are positioned between the outer polymer layer and the aluminum oxide layer. Preferably, the further aluminum oxide layer is positioned between the first additional polymer layer and the second additional polymer layer. In other words, again, the aluminum oxide layer shields the second additional polymer layer from the reference fluid.

The further aluminum oxide layer has the same thickness as the aluminum oxide layer as described above, i.e. from 40 to 60 nm, preferable 45 to 55 nm.

It is preferred that the first and second additional polymer layers are made from the same polymeric material. Preferably, that polymeric material is polyethylene terephthalate. It is preferred that the first and second additional polymer layers are bi-axially orientated, for example bi-axially orientated polyethylene terephthalate. The thickness of the first and second additional polymer layers may be of from 10 to 15 µm, preferably 11 to 13 µm.

In other words, it is preferred that bag comprises two aluminum oxide/polyethylene terephthalate layers (i.e. an aluminum oxide layer adhered to a polyethylene terephthalate layer), wherein the aluminum oxide is positioned facing the inner polymer layer. This provides an even better gas barrier.

The different layers of which the sealed bag is comprised may be adhered together by any suitable means. For example, an adhesive, such as retort adhesives may be used to attach the layers to each other. Retort adhesives are especially good at bonding to aluminum oxide and at withstanding high temperatures during high temperature curing, disinfecting and/or welding. Alternatively, the aluminum oxide layer(s) is deposited on a polymer layer by, for example, spraying. Preferably, the aluminum oxide layer is deposited on the first or second additional polymer layer. Thus, in accordance with the embodiments already described above, it is preferred that the aluminum oxide layer is deposited on a layer of polyethylene terephthalate.

Calibration of a sensor is to be understood as an experimental determination of the correspondence between sensor responses and predetermined parameter values of a reference material. The correspondence determined in the calibration is then used when a parameter in, for example, a physiological fluid is to be determined. First, a sensor response to the physiological parameter is obtained. Then, the sensor response is converted into a measured parameter value by using the correspondence determined. According to the invention, the parameter to be determined is the creatine and/or creatinine level in, for example a physiological fluid.

Quality control of a sensor is to be understood as the experimental verification that the sensor measurements are accurate and/or precise. Usually, such verification is performed by determining whether a measured parameter value of a reference material is within an acceptance range. The measured parameter value of the reference material is obtained by converting the sensor response into the measured parameter value using a calibration correspondence as described above. It is then determined whether the measured parameter value is within the acceptance range of the reference material.

The acceptance range is generally centered around a predetermined value. The limits of the range depend on, for example on sensor variation, on the variation when determining the predetermined parameter value of the reference material for both the quality control and the calibration and/or demands of accuracy and precision.

The reference fluid comprises at least one component selected from the group consisting of $CO_2$, $O_2$, $K^+$, $Na^+$, $Ca^{2+}$, $Cl^-$, glutamic acid, lactate, hemoglobin, creatinine, creatine and urea. Preferably, the reference fluid comprises at least creatine and/or creatinine.

The reference fluid may further comprise biological buffers, salts, enzymes, surfactants, chelators, antibiotics and preservatives.

The sealed bag may further comprise a sealing element which is adapted for being pierced by an access probe, such as a needle. The sealing element is preferably provided on the outside of the bag, i.e. on the outer polymer layer. The sealing element prevents leakage between the bag and the access probe when the access probe has penetrated the bag.

When the sealing element is provided on the exterior of the bag and an access probe passes through the sealing element, the movement of the access probe during piercing of the bag forces the sealing element towards the exterior wall (i.e. the outer polymer layer) of the bag and provides an even tighter sealing.

The sealing element may have a shape to make it possible to obtain a tight sealing between the access probe and the wall of the bag, and the sealing element preferably has a substantially cylindrical form that encloses the access probe. The sealing element also has a flange that abuts against the wall of the bag on the place of piercing. To obtain the desired flexibility, the sealing element is preferably made from a rubber material e.g. butyl rubber. In case of more access probes and more bags being placed in a container, more sealing elements are required. The sealing elements may be mutually connected to facilitate mounting in the container.

The sealing element is naturally attached to the bag at the location where the access probe pierces the bag, and the sealing element subsequently, by interaction with the access probe and the wall (i.e. the outer polymer layer) of the bag, seals the opening produced by the piercing. The sealing element may be attached to the outer polymer layer of the bag by means of glue or by melting of the material of the sealing element and the bag. The glue or melted material may serve as additional sealing material and provide a tighter sealing.

In an alternative preferred embodiment of the bag, according to the invention, the sealing element is attached to an access probe. In this embodiment the sealing element follows the access probe and the sealing element seals the produced opening by interaction with the access probe and the outer polymer layer of the bag. Leakage after piercing due to an imprecise placement of the sealing element on the outer surface of the bag may be avoided because the sealing element is placed on the outer surface of the bag by the access probe during piercing. The sealing element may be connected to the access probe simply by friction.

In a further alternative preferred embodiment, the sealing element is attached in a frame-like structure between the access probe and the outer polymer layer of the bag, optionally abutting the outer polymer layer of the bag. The sealing element is then attached in such a way that the access probe may easily enter the sealing element, penetrate the bag and simultaneously press the sealing element towards the outer polymer layer of the bag. The frame-like structure for holding the sealing element is preferably attached within a box-like structure holding one or more bags according to the invention.

The sealed bag may further comprise a support element attached to an inner surface of the bag. Preferably, the support element and the inner surface of the bag (i.e. the inner polymer layer) are made of the same material. Thus, the support element is preferably made from a polyolefin which is preferably polyethylene. When the support element and the inner surface are made from the same material, they may be easily joined by e.g. melting or gluing.

The support element is adapted to support the walls of the bag, e.g. during mounting in a container (described in more detail below). The support element may also serve as a support for the sealing element when the access probe penetrates the bag, whereby a very tight sealing between the sealing element and the bag is obtained.

The support element is preferably completely enclosed in the bag without penetrating the walls of the bag. More preferably, the support element is attached to an inner surface portion of the bag. The support element may be a longitudinally bar-like element having dimensions to make it fit within a bag without penetrating the walls of the bag. Moreover, the support element preferably has rounded ends to avoid damaging of the walls of the bag.

During piercing of the bag, the support element has the further function of supporting the wall of the bag and can interact with the access probe and the sealing element to obtain a very tight seal.

The support element may conveniently comprise at least one passage adapted to interact with a penetrating access probe. Preferably an inner wall in the support element forms the passage which is substantially non-deformable. The passage preferably has a diameter that exceeds the diameter of the access probe, which allows the access probe to enter the passage easily. The passage typically has a diameter being 2 to 10% larger than the diameter of the access probe. Consequently, the support element has no sealing effect. However, the support element with the passage provides for the sealing element being placed in close contact with the exterior wall of the bag (i.e. in contact with the outer polymer layer), while the interior wall (i.e. inner polymer layer) is supported by the support element in such a way that the piercing access probe forces the sealing element towards the outer wall of the bag.

The support element may comprise at least two through-going holes or bores arranged at opposite ends of the support element. This makes the support element substantially symmetric which facilitates the mounting in the bag.

Alternatively, the support element may comprise a plurality of through-going holes or bores at the respective opposite ends of the support element. This embodiment also facilitates the mounting and provides more freedom for placing the point for piercing.

In a preferred embodiment, one or both ends of the support element are provided with tongues. The one or two tongues are adapted to be cast into one or two welded joints of the bag. The embodiment provides for a more stable attachment of the support element to the bag and reduces the risk of breaching the walls of the bag due to movement of the support element, e.g. during transport of the bag.

The dimensions of the support element naturally depends on the specific use, however, a preferred length is from about 10 cm to about 22 cm, more preferably from about 13 cm to about 18 cm. Preferably the support element has a cross sectional area in the range of about 0.5 cm$^2$ to about 3 cm$^2$, more preferably from about 0.7 cm$^2$ to about 1.5 cm$^2$. The cross section of the support element may be substantially circular, oval, square, rectangular or any other desired shape.

The sealed bags according to the invention may be provided in a container. The container is preferably a box-like container having a lid and comprising one or more bags and wherein at least one of the bags contains a reference fluid for the calibration and/or quality control of a creatine and/or creatinine sensor. The container is conveniently made from a plastic material e.g. acrylonitrile-butadiene-styrene (ABS), polyethylene (PE) or polycarbonate (PC). The container e.g. includes 6-12 sealed bags. Often, one or more of the bags may contain waste or other calibration or rinse fluids.

Preferably, the bag is in the form of an envelope, which makes it easier to fit more bags into a container. Moreover, the shape of the envelope also provides for an optimal utilization of the space inside the container.

The invention also relates to a creatine and/or creatinine sensor assembly for calibration and/or quality control. The assembly comprises a sealed bag as described above, along with an access system having an access probe, and a creatine and/or creatinine sensor.

The access system comprises a sealing element and a longitudinal support element as previously described. For example, the sealing element of the access system is provided on the exterior of the sealed bag and prevents any leakage between the bag and an access probe when the access probe has penetrated the bag. The longitudinal support element provided inside the bag extends essentially parallel to an edge of the bag and is adapted to support the bag when the bag is penetrated by the access probe.

The invention also relates to a reference fluid bag assembly comprising a sealed bag according to the invention, which is adapted for being pierced by an access probe for withdrawal of the reference fluid. The assembly also comprises an access system which comprises a sealing element provided outside the bag and preventing any leakage between the bag and the access probe when the access probe has penetrated the bag, and a longitudinal support element provided inside the bag extending essentially parallel to an edge of the bag and being adapted to support the bag when the bag is penetrated by the access probe.

BRIEF DESCRIPTION OF THE FIGURES

Specific embodiments of the present invention will now be described with reference to the accompanying drawings in which.

DETAILED DESCRIPTION OF THE INVENTION

Figure 1:
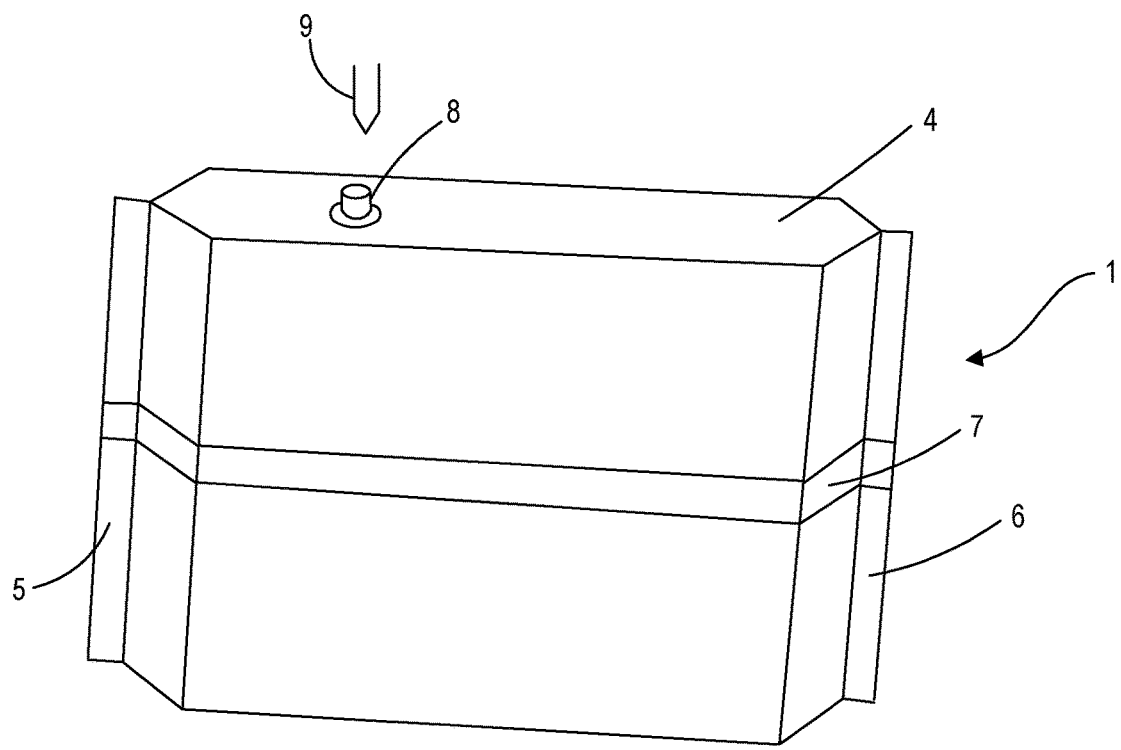
FIG. 1 illustrates a bag according to the present invention with an access system

FIG. 1 shows a simplified depiction of a sealed bag 4 according to the invention, having an access system. The sealed bag 4 with access system is a bag assembly 1. The bag assembly 1 comprises a sealed bag 4 shaped as an envelope and containing a reference fluid and a support element (not visible). The sealed bag 4 has heat-sealed joints 5, 6 at the end-parts and along the side 7 of the bag 4. The bag assembly 1 is furthermore provided with a sealing element 8 capable of sealing an opening in the bag pierced by an access probe 9 as indicated in the upper part of the figure. The access probe 9 may be connected to a lid or other element (not shown) of a container. The sealing element 8 is made from butyl rubber and the access probe is made from ABS in this specific embodiment.

Figure 2:
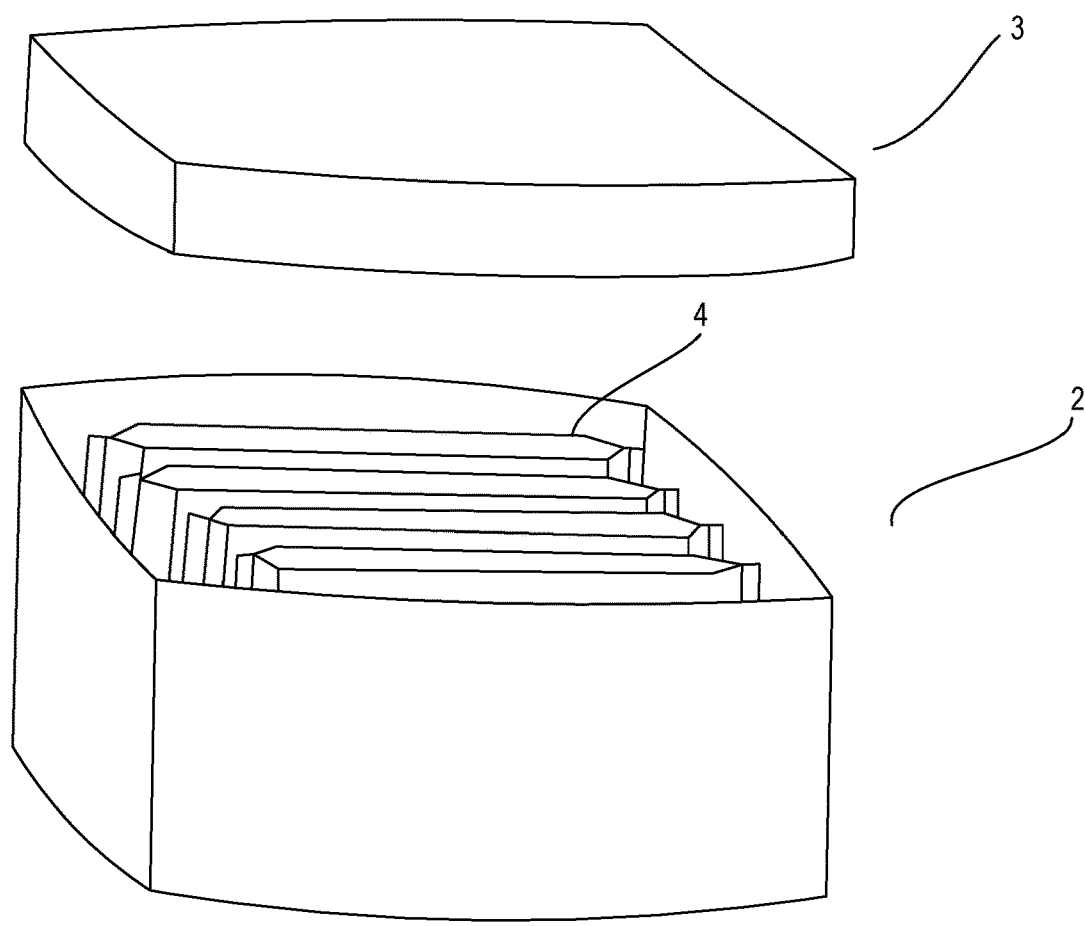
FIG. 2 illustrates a container having a plurality of bags according to the present invention.

FIG. 2 depicts a container 2 in the shape of a box-like member and lid 3. The box-like member and the lid 3 is made from ABS. The box-like member contains several sealed bags 4 of which at least one is a sealed bag 4 according to the invention. The lid 3 may comprise access probes (not shown) for piercing the sealed bags 4 and further devices (not shown) for connecting the sealed bags 4 to e.g. a creatine and/or creatinine sensor.

Figure 3:
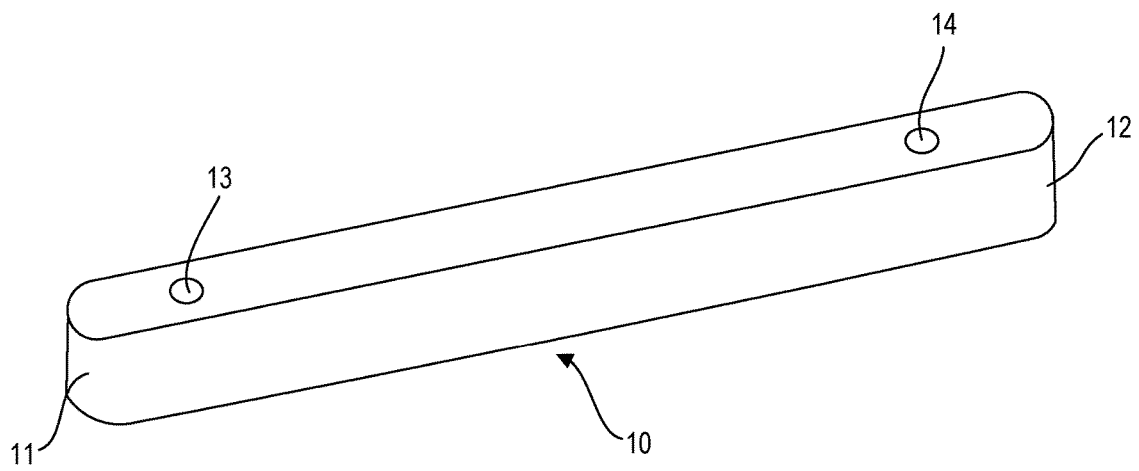
FIG. 3 illustrates an example of a support element that can be used with a bag according to the present invention.

FIG. 3 depicts a support element 10 for use in a bag assembly 1. The support element 10 is shaped as a longitudinal element with rounded ends 11, 12. Furthermore, the support element 10 is equipped with passages in the form of holes 13, 14 positioned symmetrically with respect to each end. The holes 13, 14 are intended to receive an access probe for withdrawal of reference fluid from a sealed bag. Indeed, one hole would be sufficient, however, the two holes 13, 14 positioned symmetrically with respect to each end of the support element 10 facilitate the production and mounting of the support element 10.

Figure 4:
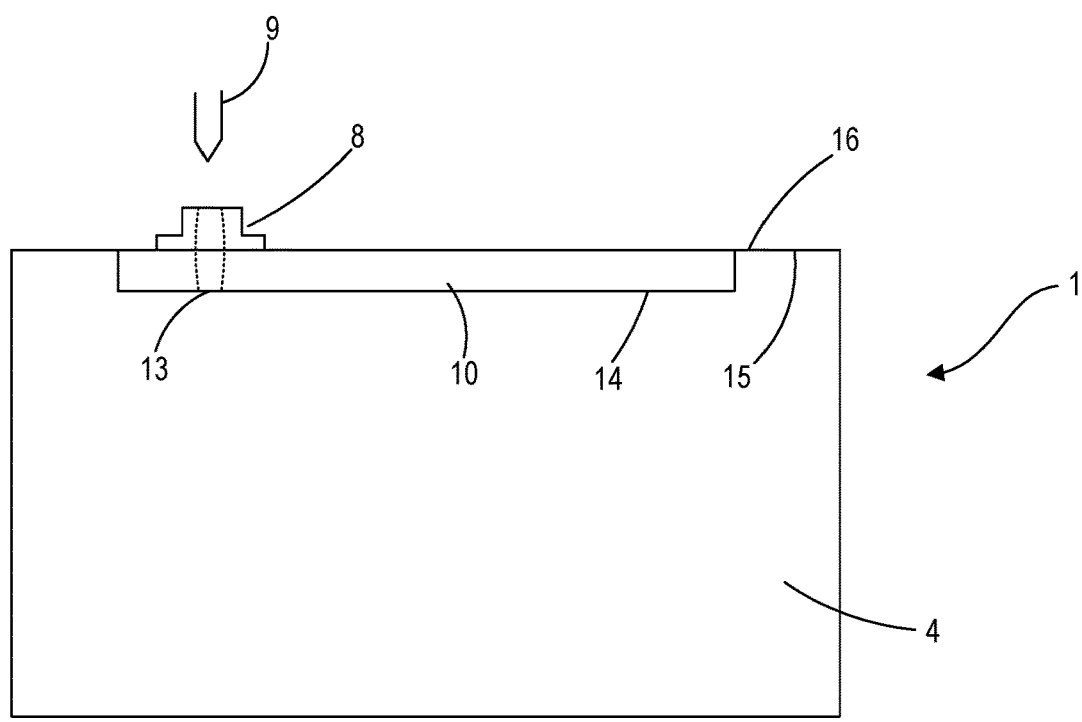
FIG. 4 illustrates a cross section of a bag according to the present invention, and having a support element and sealing element.

In FIG. 4, a support element 10 is mounted in the interior of a sealed bag 4. The support element 10 is mounted on the inner wall 15 of the sealed bag 4, such that it is in contact with the inner polymer layer. On the outer wall 16 of the sealed bag 4 is mounted a sealing element 8 at the location of the hole 13 in the support element 10.

Figure 5:
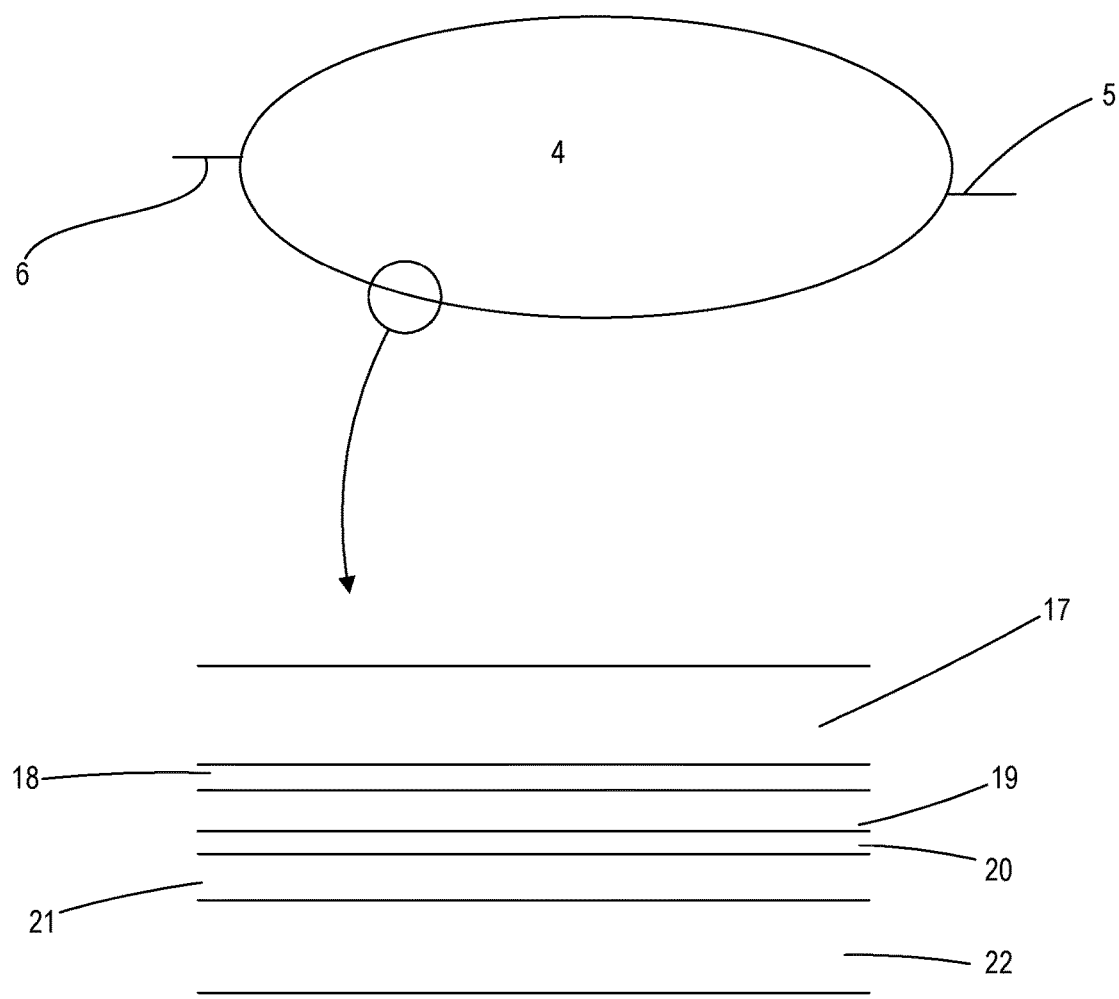
FIG. 5 illustrates a bag according to the present invention and an exploded cross-sectional view of the layers from which is bag is comprised.

FIG. 5 depicts a flexible sealed bag 4 according to the invention. Welding seams or heat-sealed seams are depicted by reference numerals 5 and 6. In more detail, FIG. 5 shows an exploded cross-sectional view of the layers from which the bag is comprised. In this embodiment, the inner polymer layer 17 is polyethylene. The inner polymer layer is adjacent to aluminum oxide layer 18. The first additional polymer layer 19 and second additional polymer layer 21 is made from polyethylene terephthalate. As shown, the second additional polymer layer 21 and a further additional aluminum oxide layer 20 is positioned between the outer polymer layer 22 and the first additional polymer layer 19. Further, the further aluminum oxide layer 20 is positioned between the first additional polymer layer 19 and the second additional polymer layer 21. In this way, the aluminum oxide layer is never on the outside or the inside of the bag, so as to prevent damage of the aluminum oxide. The provision of the additional first and second polymer layers serve to protect the aluminum oxide layers.

EXAMPLES

Tests were carried out to compare a sealed reference fluid bag having an aluminum foil layer (i.e. a bag not according to the invention) with a sealed reference bag having an aluminum oxide layer (i.e. a bag according to the invention). One particular parameter tested was sensitivity to creatinine (sCrn), which parameter is important in establishing the concentration of creatinine in a given sample.

Figure 6:
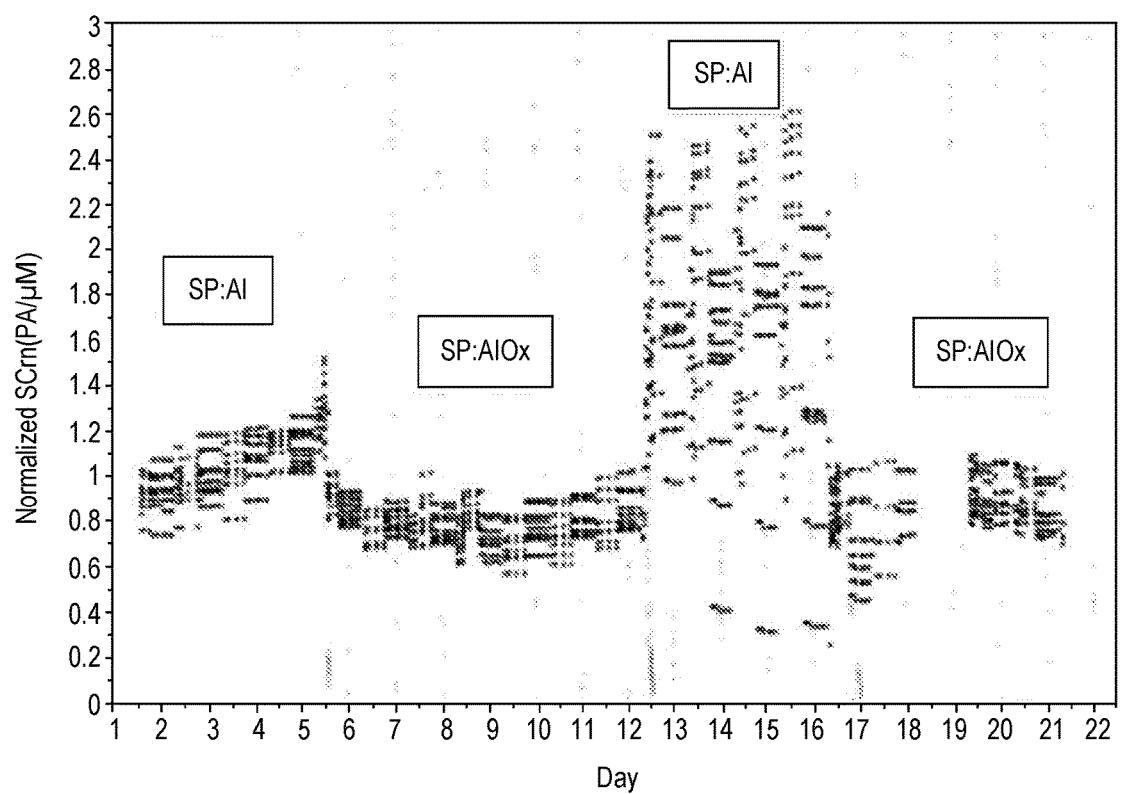
FIG. 6 is a plot normalized sensitivity for creatinine (sCrn) vs. time measured on Cal2 (a calibration solution containing creatinine, but no creatine) for a sealed reference fluid bag having an aluminum gas barrier layer (SP: Al) and for a sealed reference fluid bag having an aluminum oxide gas barrier layer (SP: AlOx).

FIG. 6 shows the measurement of normalized sCrn over time using a bag according to the invention (SP: AlOx), and using a comparative bag having an aluminum layer (SP: Al). As depicted along the x-axis of FIG. 6, sCrn was measured over 22 days.

The study began by measuring sCrn for a period of 5 days using the comparative bag having an aluminum layer. It can be seen that the normalized sCrn was fairly consistent over this period. The comparative bag was then set aside. For the next 7 days, a bag according to the invention having an aluminum oxide layer was used to measure sCrn. Again, the normalized sCrn was fairly consistent. However, when the comparative bag (i.e. as used on days 1 to 5) was used for days 13 to 17, it can be seen that the normalized sCrn was highly inconsistent (this is depicted by the wide spread of normalized sCrn values). Thus, this experiment shows that, over time, the consistency of the normalized sCrn obtained using the comparative bag having an aluminum layer deteriorates significantly. In contrast, when the sCrn measurement was obtained for the next 5 days (i.e. days 18 to 22) using the bag having an aluminum oxide layer (i.e. the same bag used on days 6 to 12), the normalized sCrn remains consistent.

In summary, FIG. 6 shows that the normalized measured value of sCrn is substantially consistent over time when determined using a bag according to the invention. In contrast, the measured value of sCrn varies widely over time when determined using a comparative bag having an aluminum layer.

Thus, the consistency of the normalized sCrn parameter for a reference fluid bag having an aluminum oxide layer is much improved compared to that of the bag having an aluminum layer. Thus, a reference fluid bag according to the invention results in improved calibration and/or quality control.

It is to be understood that the present disclosure includes permutations of combinations of the optional features set out in the embodiments described above. In particular, it is to be understood that the features set out in the appended dependent claims are disclosed in combination with any other relevant independent claims that may be provided, and that this disclosure is not limited to only the combination of the features of those dependent claims with the independent claim from which they originally depend.

The invention claimed is:

1. A sealed bag comprising:
   an inner polymer layer having an inner surface and an outer surface;
   an outer polymer layer;
   an aluminum oxide gas barrier layer between the inner polymer layer and the outer polymer layer and adjacent to the outer surface of the inner polymer layer; and
   a reference fluid in contact with the inner surface of the inner polymer layer, the reference fluid comprising at least one component selected from the group consisting of $CO_2$, $O_2$, $K^+$, $Na^+$, $Ca^{2+}$, $Cl^-$, glutamic acid, lactate, hemoglobin, creatinine, creatine and urea.

2. The sealed bag according to claim 1, further comprising a first additional polymer layer between the inner polymer layer and outer polymer layer.

3. The sealed bag according to claim 2, wherein the first additional polymer layer is positioned between the outer polymer layer and the aluminum oxide layer.

4. The sealed bag according to claim 2, further comprising a second additional polymer layer and a further aluminum oxide layer, wherein the second additional polymer layer and further aluminum oxide layer are positioned between the outer polymer layer and the first additional polymer layer.

5. The sealed bag according to claim 4, wherein the further aluminum oxide layer is positioned between the first additional polymer layer and the second additional polymer layer.

6. The sealed bag according to claim 4, wherein the further aluminum oxide layer has a thickness of from 40 to 60 nm.

7. The sealed bag according to claim 4, wherein the second additional polymer layer has a thickness of from 10 to 15 μm.

8. The sealed bag according to claim 4, wherein the second additional polymer layer is polyethylene terephthalate.

9. The sealed bag according to claim 4, wherein the second additional polymer layer is a bi-axially orientated polymer.

10. The sealed bag according to claim 2, wherein the first additional polymer layer is polyethylene terephthalate.

11. The sealed bag according to claim 2, wherein the first additional polymer layer has a thickness of from 10 to 15 μm.

12. The sealed bag according to claim 2, wherein the first additional polymer layer is a bi-axially orientated polymer.

13. The sealed bag according to claim 1, wherein the inner polymer layer is a polyolefin.

14. The sealed bag according to claim 13, wherein the polyolefin is polyethylene or polypropylene.

15. The sealed bag according to claim 1, wherein the outer polymer layer is bi-axially orientated polyamide.

16. The sealed bag according to claim 1, wherein the aluminum oxide layer has a thickness of from 40 to 60 nm.

17. The sealed bag according to claim 1, wherein the inner polymer layer has a thickness of from 70 to 90 μm.

18. The sealed bag according to claim 1, wherein the outer polymer layer has a thickness of from 10 to 20 μm.

19. The sealed bag according to claim 1, wherein the inner polymer layer is a bi-axially orientated polymer.

20. The sealed bag according to claim 1, wherein the reference fluid comprises creatine or creatinine.

21. The sealed bag according to claim 1, further comprising a sealing element adapted for being pierced by an access probe.

22. The sealed bag according to claim 1, further comprising a support element attached to the inner surface of the inner polymer layer.

23. The sealed bag according to claim 22, wherein the support element and the inner polymer layer are made from the same material.

24. The sealed bag according to claim 22, wherein the support element comprises at least one passage for receiving an access probe.

25. A reference fluid bag assembly comprising:

a sealed bag according to claim 1;

an access system;

wherein the access system comprises:

a sealing element provided outside the bag for preventing leakage of fluid between the bag and an access probe when the access probe has penetrated the bag, and a longitudinal support element provided inside the bag extending essentially parallel to an edge of the bag, wherein to support the bag when the bag is penetrated by the access probe.

* * * * *